United States Patent [19]

Kinsho et al.

[11] Patent Number: 5,582,765
[45] Date of Patent: Dec. 10, 1996

[54] TRIFLATE COMPOUNDS AND PROCESS FOR PREPARING SILACYCLOHEXANE-BASED LIQUID CRYSTAL COMPOUNDS FROM THE TRIFLATE COMPOUNDS

[75] Inventors: Takeshi Kinsho; Takaaki Shimizu; Tsutomu Ogihara; Tatsushi Kaneko; Mutsuo Nakashima, all of Niigata-ken, Japan

[73] Assignee: Shin-Etsu Chemical Co., Ltd., Tokyo, Japan

[21] Appl. No.: 511,276

[22] Filed: Aug. 4, 1995

[30] Foreign Application Priority Data

Aug. 5, 1994  [JP] Japan .................................. 6-204661

[51] Int. Cl.$^6$ ............................ C09K 19/34; C09K 19/30; C07F 7/08
[52] U.S. Cl. ............................. 252/299.61; 252/299.63; 252/299.66; 556/406
[58] Field of Search .................. 252/299.61, 299.63, 252/299.66; 556/406

[56] References Cited

U.S. PATENT DOCUMENTS 5,426,206  6/1995  Jung et al. ........................ 556/406
5,454,977  10/1995  Shimizu et al. ................... 252/299.61
5,498,737  3/1996  Ogihara et al. ...................... 556/406

FOREIGN PATENT DOCUMENTS 6135862  5/1994  Japan .

*Primary Examiner*—Shean C. Wu
*Attorney, Agent, or Firm*—Lowe, Price, LeBlanc & Becker

[57] ABSTRACT

A triflate compound of the following general formula is provided

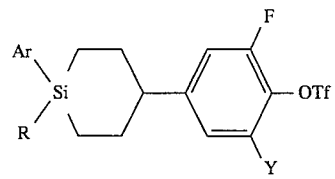

wherein Ar represents a phenyl group or a tolyl group, R represents a phenyl group, a tolyl group, a linear alkyl group having from 1 to 10 carbon atoms, a mono or difluoroalkyl group having from 1 to 10 carbon atoms, a branched alkyl group having from 3 to 8 carbon atoms, an alkoxyalkyl group having from 2 to 7 carbon atoms and an alkenyl group having from 2 to 8 carbon atoms, Tf represents a trifluoromethanesulfonyl group, and Y represents H or F. A process for preparing silacyclohexane-based liquid crystal compounds from the triflate compound is also described.

7 Claims, No Drawings

TRIFLATE COMPOUNDS AND PROCESS FOR PREPARING SILACYCLOHEXANE-BASED LIQUID CRYSTAL COMPOUNDS FROM THE TRIFLATE COMPOUNDS

BACKGROUND OF THE INVENTION

1. Field of the Invention

This invention relates to a novel triflate compound and also to a process for preparing silacyclohexane-based liquid crystal compounds from the triflate compounds.

2. Description of the Prior Art

The liquid crystal display devices make use of optical anisotropy and dielectric anisotropy of liquid crystal substances. Depending on the mode of display, there are a variety of display systems including those of a twisted nematic type (TN type), a supertwisted nematic type (STN type), a super birefringence type (SBE type), a dynamic scattering type (DS type), a guest/host type, a type of deformation of aligned phase (DAP type), a polymer dispersion type (PD type), and an optical mode interference type (OMI type). The most popular display device is one which is based on the Schadt-Helfrich effect and has a twisted nematic structure.

Although the properties of the liquid crystal substances used in these liquid crystal devices depend, more or less, on the type of display, it is commonly required that the liquid crystal substances have a wide range of liquid crystal working temperatures and that they be stable against moisture, air, light, heat, electric field and the like. Moreover, the liquid crystal substances should desirably be low in viscosity and should ensure a short address time, a low threshold voltage and a high contrast in a cell.

As the liquid crystal display devices have wider utility in recent years, the characteristic properties required for liquid crystal materials become much severer. In addition, those characteristics which have never been required for conventional liquid crystal substances are now expected such as a lower drive voltage, a wider working temperature range which could satisfy the on-vehicle needs and an improvement in low temperature performance.

Under these circumstances, we developed novel liquid crystal compounds which contain a silicon atom in the molecule so that the characteristic properties for use as a liquid crystal substance are improved. These liquid crystal compounds have been proposed, for example, in co-pending U.S. application Ser. Nos. 08/377,961, filed Jan. 25, 1995 now U.S. Pat. No. 5,498,737 and 08/395,706, filed Feb. 28, 1995 (corresponding to European Patent Application Nos. 95101167.5, filed Jan. 27, 1995 and 951029.8.1, filed Mar. 1, 1995 and Korean Patent Application Nos. 95-1701, filed Jan. 28, 1995 and 95-4084, filed Feb. 28, 1995, respectively).

SUMMARY OF THE INVENTION

It is an object of the invention to provide a novel triflate compound which is an intermediate compound useful for preparing silacyclohexane-based liquid crystal compounds of the type which has a fluorine substitution (i.e. a so-called lateral fluorine substitution) on an aromatic ring.

It is another object of the invention to provide a process for preparing a silacyclohexane-based liquid crystal compound which is a kind of derivative obtained from the triflate compound.

It will be noted that in order to introduce an intended number of fluorine substituent or substituents on the intended position or positions of an aromatic ring, it is preferred to constitute a final molecular skeletal structure by use of a synthetic intermediate which has the fluorine substituent or substituents at the intended positions on comparison with the case wherein the fluorine substituent or substituents are introduced after arrangement of a final molecular skeletal structure. Such a synthetic intermediate should favorably be prepared from industrially, readily available starting materials and we have strongly demanded the synthetic intermediate as having high general-purpose capabilities of being derived into various types of silacyclohexane-based liquid crystal compounds.

Accordingly, a still further object of the invention is to provide an intermediate compound which meets the above demand.

The above objects can be achieved, according to one embodiment of the invention, by a triflate compound of the following formula (I)

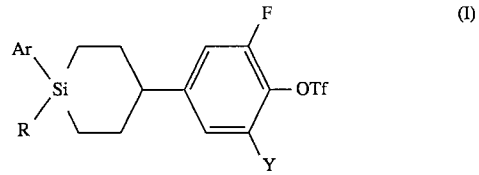

wherein Ar represents a phenyl group or a tolyl group, R represents a phenyl group, a tolyl group, a linear alkyl group having from 1 to 10 carbon atoms, a mono or difluoroalkyl group having from 1 to 10 carbon atoms, a branched alkyl group having from 3 to 8 carbon atoms, an alkoxyalkyl group having from 2 to 7 carbon atoms or an alkenyl group having from 2 to 8 carbon atoms, Tf represents a trifluoromethanesulfonyl group, and Y represents H or F.

The triflate compound of the formula (I) is useful as an intermediate for preparing silacyclohexane-based liquid crystal compound of the following general formula (A)

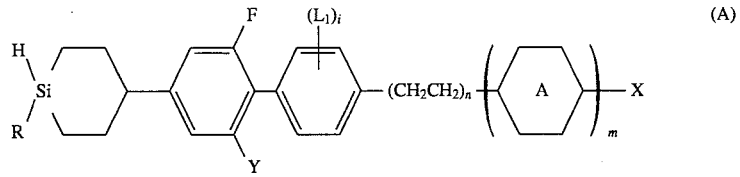

wherein R represents a phenyl group or a tolyl group, a linear alkyl group having from 1 to 10 carbon atoms, a mono or difluoroalkyl group having from 1 to 10 carbon atoms, a branched alkyl group having from 3 to 8 carbon atoms or an alkoxyalkyl group having from 2 to 7 carbon atoms or an alkenyl group having from 2 to 8 carbon atoms,

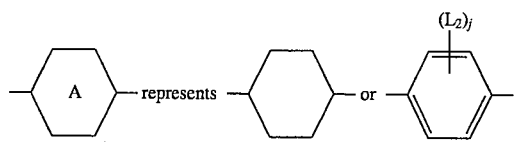

in which $L_2$ represents a halogen, preferably F, or $CH_3$, and j is a value of 0, 1 or 2, X represents R or OR, in which R has the same meaning as defined above, CN, F, Cl, Br, $CF_3$, $OCF_3$, $OCHF_2$, $OCHFCl$, $OCF_2Cl$, $CF_2Cl$, $CHFCl$, $(O)m_1CY_1=CX_1CX_2$, in which m1 is a value of 0 or 1, $Y_1$ and $X_1$ independently represent H, F or Cl, and $X_2$ represents F or Cl, or $O(CH_2)_r(CF_2)_sX_3$, in which r and s are, respectively, a value of 0, 1 or 2 provided that r+s=2,3 or 4, and $X_3$ represents H, F or Cl, Y represents H or F, $L_1$ represents the same meaning as $L_2$ and represents a halogen or $CH_3$, n and m independently represents a value of 0 or 1, and i is a value of 0,1 or 2.

More specifically, the liquid crystal compounds of the general formula (A) include those compounds of the following general formulas (II) to (V):

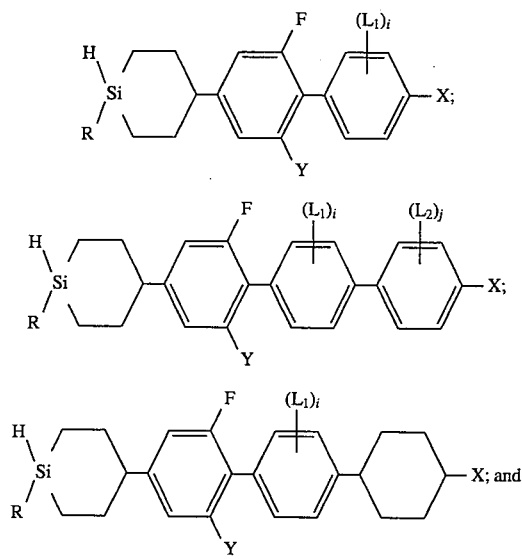

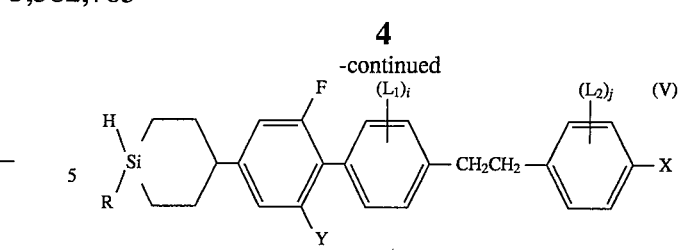

wherein R, Y, $L_1$, j, X, $L_2$, and i have, respectively, the same meanings as defined above.

The liquid crystal compound of the general formula (A) is prepared using the triflate compound of the general formula (I) according to a process which comprises:

subjecting the triflate compound of the general formula (I) to reaction with an organometallic compound or reagent of the following general formula (1) in the presence of a transition metal catalyst

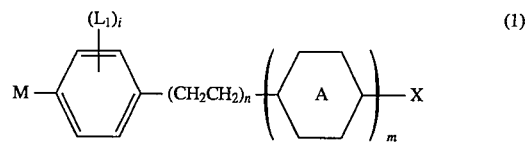

wherein

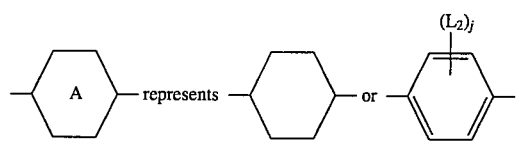

in which $L_2$ represents a halogen, preferably F, or $CH_3$, and j is a value of 0,1 or 2, M represents ZnP in which P represents a halogen, preferably Cl, Br or I, $Sn(CH_2CH_2CH_2CH_3)_3$ or $Sn(CH_3)_3$, X represents R or OR, in which R has the same meaning as defined hereinbefore, CN, F, Cl, Br, $CF_3$, $OCF_3$, $OCHF_2$, $OCHFCl$, $OCF_2Cl$, $CF_2Cl$, $CHFCl$, $(O)m_1CY_1=CX_1CX_2$, in which m1 is a value of 0 or 1, $Y_1$ and $X_1$ independently represent H, F or Cl, and $X_2$ represents F or Cl, or $O(CH_2)_r(CF_2)_sX_3$, in which r and s are, respectively, a value of 0, 1 or 2 provided that r+s=2,3 or 4, and $X_3$ represents H, F or Cl, $L_1$ represents a halogen, preferably F, or $CH_3$, n and m are, respectively, a value of 0 or 1, and i is a value of 0, 1 or 2, thereby obtaining a compound of the following general formula (2)

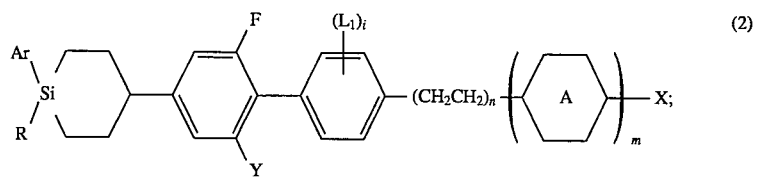

and subjecting the compound of the formula (2) to de-silylation and then to reduction to obtain a compound of the formula (A)

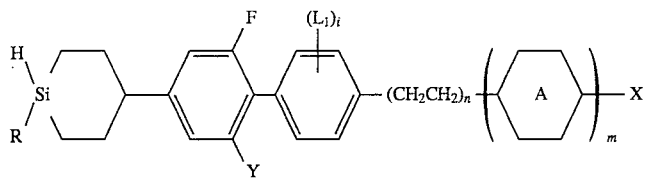

(A)

DETAILED DESCRIPTION OF THE INVENTION

A triflate compound of the present invention is a novel compound of the following general formula (1)

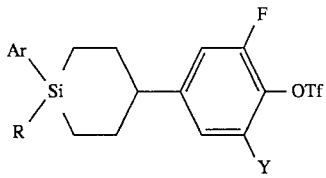

(I)

wherein Ar represents a phenyl group or a tolyl group, R represents a phenyl group, a tolyl group, a linear alkyl group having from 1 to 10 carbon atoms, a mono or difluoroalkyl group having from 1 to 10 carbon atoms, a branched alkyl group having from 3 to 8 carbon atoms, an alkoxyalkyl group having from 2 to 7 carbon atoms or an alkenyl group having from 2 to 8 carbon atoms, Tf represents a trifluoromethanesulfonyl group, and Y represents H or F.

Specific examples of the linear alkyl group having from 1 to 10 carbon represented by R include methyl, ethyl, n-propyl, n-butyl, n-pentyl, n-hexyl, n-heptyl, n-octyl, n-nonyl and n-decyl. Specific examples of the mono or difluoroalkyl group having from 1 to 10 carbon atoms include fluoromethyl, 1-fluoroethyl, 1-fluoropropyl, 1-fluorobutyl, 1-fluoropentyl, 1-fluorohexyl, 1-fluoroheptyl, 1-fluorooctyl, 1-fluorononyl, 1-fluorodecyl, 2-fluoroethyl, 2-fluoropropyl, 2-fluorobutyl, 2-fluoropentyl, 2-fluorohexyl, 2-fluoroheptyl, 2-fluorooctyl, 2-fluorononyl, 2-fluorodecyl, 3-fluoropropyl, 3-fluorobutyl, 3-fluoropentyl, 3-fluorohexyl, 3-fluoroheptyl, 3-fluorooctyl, 3-fluorononyl, 3-fluorodecyl, 4-fluorobutyl, 4-fluoropentyl, 4-fluorohexyl, 4-fluoroheptyl, 4-fluorooctyl, 4-fluorononyl, 4-fluorodecyl, 5-fluoropentyl, 5-fluorohexyl, 5-fluoroheptyl, 5-fluorooctyl, 5-fluorononyl, 5-fluorodecyl, 6-fluorohexyl, 6-fluoroheptyl, 6-fluorononyl, 6-fluorodecyl, 7-fluoroheptyl, 7-fluorooctyl, 7-fluorononyl, 7-fluorodecyl, 8-fluorocotyl, 8-fluorononyl, 8-fluorodecyl, 9-fluorononyl, 9-fluorodecyl, 10-fluorodecyl, difluoromethyl, 1,1-difluoroethyl, 1,1-difluoropropyl, 1,1-difluorobutyl, 1,1-difluoropentyl, 1,1-difluorohexyl, 1,1-difluoroheptyl, 1,1-difluorooctyl, 1,1-difluorononyl, 1,1-difluorodecyl, 2,2-difluoroethyl, 2,2-difluoropropyl, 2,2-difluorobutyl, 2,2-difluoropentyl, 2,2-difluorohexyl, 2,2-difluoroheptyl, 2,2-difluorooctyl, 2,2-difluorononyl, 2,2-difluorodecyl, 3,3-difluoropropyl, 3,3-difluorobutyl, 3,3-difluoropentyl, 3,3-difluorohexyl, 3,3-difluoroheptyl, 3,3-difluorooctyl, 3,3-difluorononyl, 3,3-difluorodecyl, 4,4-difluorobutyl, 4,4-difluoropentyl, 4,4-difluorohexyl, 4,4-difluoroheptyl, 4,4-difluorooctyl, 4,4-difluorononyl, 4,4-difluorodecyl, 5,5-difluoropentyl, 5,5-difluorohexyl, 5,5-difluoroheptyl, 5,5-difluorooctyl, 5,5-difluorononyl, 5,5-difluorodecyl, 6,6-difluorohexyl, 6,6-difluoroheptyl, 6,6-difluorooctyl, 6,6-difluorononyl, 6,6-difluorodecyl, 7,7-difluoroheptyl, 7,7-difluorooctyl, 7,7-difluorononyl, 7,7-difluorodecyl, 8,8-difluorooctyl, 8,8-difluorononyl, 8,8-difluorodecyl, 9,9-difluorononyl, 9,9-difluorodecyl and 10,10-difluorodecyl.

Specific examples of the branched alkyl group having 3 to 8 carbon atoms include isopropyl, 1-methylpropyl, 2-methylpropyl, sec-butyl, isobutyl, 1-methylbutyl, 2-methylbutyl, 3-methylbutyl, 1-methylpentyl, 2-methylpentyl, 3-methylpentyl, 1-ethylpentyl, 1-methylhexyl, 2-methylhexyl, 3-methylhexyl, 2-ethylhexyl, 3-ethylhexyl, 1-methylheptyl, 2-methylheptyl and 3-methylheptyl.

Specific examples of the alkoxyalkyl group having from 2 to 7 carbon atoms include methoxymethyl, ethoxymethyl, propoxymethyl, butoxymethyl, pentoxymethyl, hexyloxymethyl, methoxyethyl, ethoxyethyl, propoxyethyl, butoxyethyl, methoxypropyl, ethoxypropyl, propoxypropyl, butoxypropyl, methoxybutyl, ethoxybutyl, propoxybutyl, methoxypentyl and ethoxypentyl.

Specific examples of the alkenyl group include vinyl, 1-propenyl, allyl, 1-butenyl, 3-butenyl, isoprenyl, 1-pentenyl, 3-pentenyl, 4-pentenyl, dimethylallyl, 1-hexenyl, 3-hexenyl, 5-hexenyl, 1-heptenyl, 3-heptenyl, 6-heptenyl and 7-octenyl.

Of these, preferred linear alkyl groups are ones having from 3 to 7 carbon atoms and include, for example, n-propyl, n-butyl, n-pentyl, n-hexyl and n-heptyl. Likewise, preferred mono or difluoroalkyl groups include 2-fluoroethyl, 2-fluoropropyl, 2-fluorobutyl, 2-fluoropentyl, 2-fluorohexyl, 2-fluoroheptyl, 4-fluorobutyl, 4-fluoropentyl, 4-fluorohexyl, 4-fluoroheptyl, 5-fluoropentyl, 6-fluorohexyl, 7-fluoroheptyl, 2,2-difluoroethyl, 2,2-difluoropropyl, 2,2-difluorobutyl, 2,2-difluoropentyl, 2,2-difluorohexyl, 2,2-difluoroheptyl, 4,4-difluorobutyl, 4,4-difluoropentyl, 4,4-difluorohexyl, 4,4-difluoroheptyl, 5,5-difluoropentyl, 5,5-difluorohexyl, 5,5-difluoroheptyl, 6,6-difluorohexyl, 6,6-difluoroheptyl and 7,7-difluoroheptyl.

Preferred branched alkyl groups include, for example, isopropyl, 1-methylpentyl, 2-methylpentyl, 1-methylbutyl, 2-methylbutyl, 3-methylbutyl, 1-methylpentyl and 2-ethylhexyl.

Preferred alkoxyalkyl groups include methoxymethyl, methoxyethyl, methoxypropyl, methoxypentyl, ethoxymethyl, ethoxyethyl, propoxymethyl and pentoxymethyl. Those alkenyl groups mentioned hereinbefore are all preferably used.

The compound of the formula (I) is readily prepared from a silacyclohexanone compound of the following general formula (3) which we proposed in Japanese Patent Application No. 6-71825, filed Mar. 24, 1994 and not yet laid open

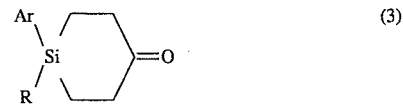

(3)

wherein Ar and R have, respectively, the same meanings as defined hereinabove.

More particularly, according to the following reaction sequence (4), an organometallic reagent which is prepared from a commercially available, fluorine atom-bearing bromophenol compound and whose phenolic hydroxyl group is protected with a silyl group is reacted with the silacyclohexanone compound of the formula (3) to obtain an alcohol compound, followed by dehydration, catalytic reduction, elimination of the protective group and final trifluoromethanesulfonylation (triflation)

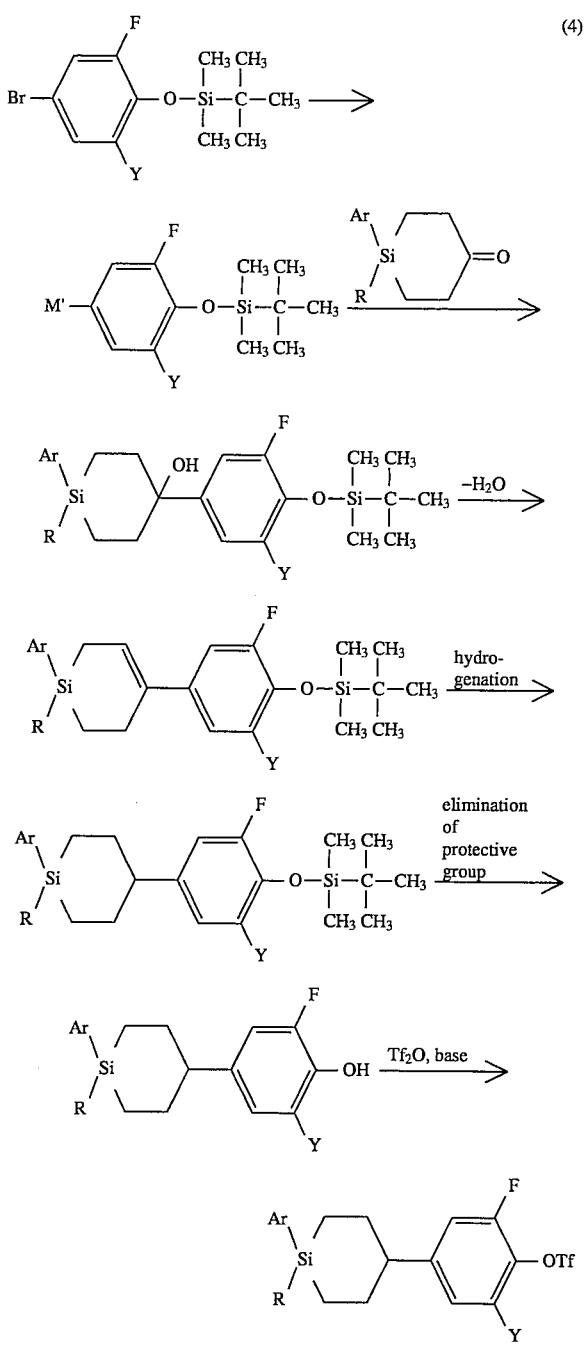

wherein Ar, R, Y and Tf have, respectively, the same meanings as defined hereinbefore, and M' represents Li or MgP in which P represents a halogen, preferably Cl, Br or I.

In the first step, the use of either a Grignard reagent or an organolithium reagent as an organometallic reagent permits the reaction with the silacyclohexanone to proceed in high yield. This reaction is preferably effected under conditions of a temperature ranging from 0° to 150° C. and a time ranging from 3 to 8 hours.

The resultant compound is subjected to dehydration by use of acids or salts thereof. Examples of the acids or salts include inorganic acid such as hydrochloric acid, sulfuric acid, nitric acid and the like and salts thereof, and organic acids such as p-toluenesulfonic acid, camphorsulfonic acid, trifluoroacetic acid and the like. In order to quickly remove generated water, hydrocarbons such as benzene, toluene, xylene, cumene, hexane, iso-octane and the like are used for the reaction. Eventually, the reaction is permitted to proceed more rapidly under azeotropic conditions. In this sense, the reaction should be effected under refluxing conditions.

Then, the resultant product is subjected to hydrogenation or catalytic reduction in an atmosphere of hydrogen ranging from an atmospheric pressure of hydrogen to 20 kg/cm² in the presence of a catalyst. Examples of such a catalyst include palladium, platinum, rhodium, nickel, ruthenium and the like.

Subsequently, the silyl protective group is eliminated. The elimination is performed by hydrolysis with acids or acidic substances such as acetic acid, hydrochloric acid, sulfuric acid, boron trifluoride, acidic ion exchange resins and the like. Alternatively, the elimination may be effected by use of hydrofluoric acid or salts thereof. The elimination is effected by a usual manner.

Finally, the thus eliminated product is subjected to triflation with trifluoromethanesulfonic anhydride by use of a base. Preferred examples of the base include pyridine, triethylamine, tri-n-butylamine, diisopropylethylamine, N,N-dimethylaniline, 4-dimethylaminopyridine and the like tertiary amines. This trifluormethanesulfonation reaction is preferably carried out under conditions of a temperature ranging from 0° to 150° C. and a time ranging from 3 to 8 hours.

In this manner, the triflate compound of the general formula (I) of the invention is obtained. This compound is useful for preparing various types of silacyclohexane-based liquid crystal compounds.

The preparation of silacyclohexane-based liquid crystal compounds which are derivatives of the triflate compound (I) is described below The triflate compound of the general formula (I) is subjected to coupling reaction with an organozinc reagent or an organotin reagent, which can be prepared from a corresponding halide by a usual manner, in the presence of a transition metal catalyst according to the following reaction formula (5)

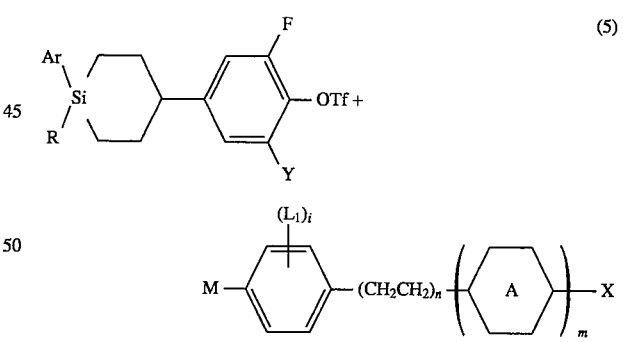

wherein

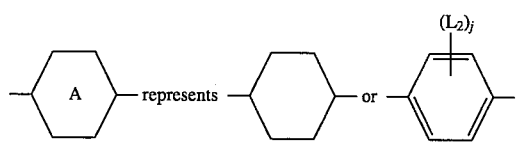

in which $L_2$ represents a halogen, preferably F, or $CH_3$, and j is a value of 0,1 or 2, M represents ZnP in which P represents a halogen, preferably Cl, Br or I, $Sn(CH_2CH_2CH_2CH_3)_3$ or $Sn(CH_3)_3$, X represents R or OR, in which R have the same meanings as defined hereinbefore, CN, F, Cl Br, $CF_3$, $OCF_3$, $OCHF_2$, OCHFCl, $OCF_2Cl$, $CF_2Cl$, CHFCl, $(O)m_1CY_1=CX_1CX_2$, in which m1 is a value of 0 or 1, $Y_1$ and $X_1$ independently represent H, F or Cl, and $X_2$ represents F or Cl, or $O(CH_2)_r(CF_2)_sX_3$, in which r and s are, respectively, a value of 0, 1 or 2 provided that r+s=2,3 or 4, and $X_3$ represents H, F or Cl, $L_1$ represents a halogen, preferably F or $CH_3$, n and m are, respectively, a value of 0 or 1, and i is a value of 0, 1 or 2, thereby obtaining a compound of the following general formula (2)

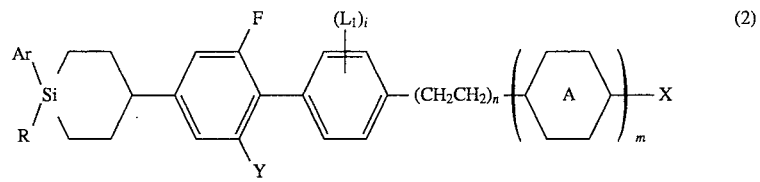
(2)

The above coupling reaction is effected in the presence of a transition metal catalyst preferably under conditions of a temperature ranging from 0° to 150° C. Preferred examples of the transition metal catalyst include palladium compounds. The palladium catalysts include, for example, zero valent palladium compounds such as tetrakis(triphenylphosphine)palladium (0), di-[1,2-bis(diphenylphosphino)ethane]palladium (0) and the like, compounds consisting of divalent palladium compounds, such as palladium acetate, palladium chloride, [1,1-bis(diphenylphosphino)ferrocene]palladium (II) chloride and the like, and combinations of those compounds mentioned above with reducing agents.

The coupling reaction is facilitated on addition, to the reaction system, of lithium salts such as lithium chloride, lithium bromide, lithium iodide and the like. By the addition, the reaction proceeds in high yield for both cases using the organozinc and organotin reagents. The lithium salt is preferably added in an amount of from 0.1 to 3 moles per mole of the triflate compound.

Thereafter, the resultant reaction product is subjected to de-silylation reaction with an electrophilic reagent to provide a halosilacyclohexane compound, followed by reduction reaction according to the following reaction sequence (6)

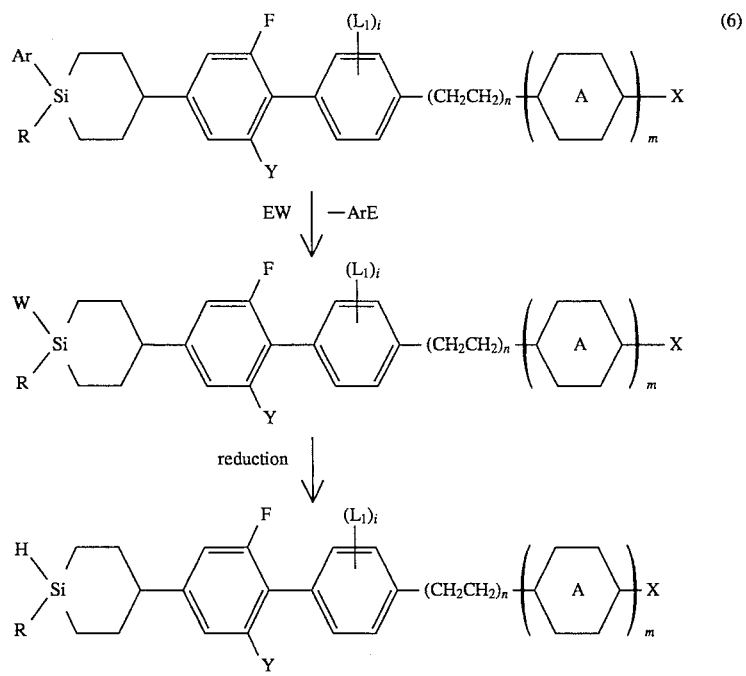

wherein EW represents an electrophilic reagent in which W represents a halogen and preferably Cl, I or Br.

The electrophilic reagents include, for example, halogens, hydrogen halides, metal halides, sulfonic derivatives, acid halides, alkyl halides and the like. Preferable examples include iodine, bromine, chlorine, iodine monochloride, hydrogen chloride, hydrogen bromide, hydrogen iodide, mercury (II) chloride, trimethylsilyl chlorosulfonate, acetyl chloride, acetyl bromide, benzoyl chloride, t-butyl chloride and the like. In order to increase the reaction velocity, addition of Lewis acids such as aluminium chloride, zinc chloride, titanium tetrachloride, boron trifluoride and the like or irradiation of visible light or UV light is effective. The de-silylation reaction may be effected in a wide range of temperature. The reaction temperature is preferably in the range of from 0° to 80° C., more preferably from 10° to 40° C. The electrophilic reagent is preferably used at a ratio by mole between the cyclohexanone compound and the electrophilic reagent of 1:1 to 1:5, more preferably 1:1 to 1:2.

The reagents used for the reduction of the resultant halosilacyclohexane compound include, for example, metal hydrides such as sodium hydride, potassium hydride, trialkylsilanes, boranes, dialkylaluminium compounds and the like, complex hydrides such as lithium aluminium hydride, sodium borohydride, lithium borohydride, potassium borohydride, tributylammonium borohydride and the like, and substituted hydrides thereof such as lithium trialkoxyaluminium hydrides, sodium di(methoxyethoxy)aluminium hydride, lithium triethylborohydride, sodium cyanoborohydride and the like.

Although not limitative, the reduction of the halosilacyclohexane is carried out preferably at a temperature of from 0° to 150° C., more preferably from 20° to 100° C.

By the above process, silacyclohexane-based liquid crystal compounds of the general formula (A) can be prepared. These compounds may be used as a liquid crystal as they are or after separation into an intended trans, trans form of the compound by a usual manner such as recrystallization or chromatography.

As will be apparent from the foregoing reaction formula (5), various types of silacyclohexane-based liquid crystal compounds can be obtained. For instance, when an organometallic reagent of the following general formula (7) wherein n and m are, respectively, zero in the formula (1) indicated hereinbefore is used

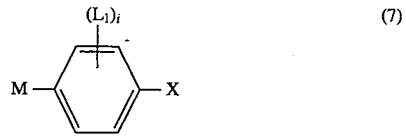
(7)

wherein M, Li, i and X have, respectively, the same meanings as defined hereinbefore, the silacyclohexane-based compound of the foregoing formula (II) is obtained through a series of the steps set out with respect to the compound (A).

Likewise, when the organometallic reagent of the afore-indicated general formula (1) wherein n=0 and m is 1 and

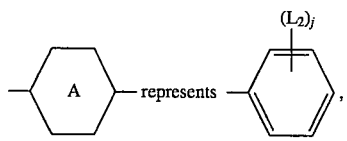

the silacyclohexane-based compound of the foregoing formula (III) can be obtained.

When the organometallic reagent of the afore-indicated general formula (1) is used wherein n=0, m is 1 and

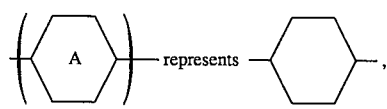

the silacyclohexane-based compound of the foregoing formula (IV) can be obtained.

Moreover, when the organometallic reagent of the afore-indicated general formula (1) is used wherein n=1, m is 1 and

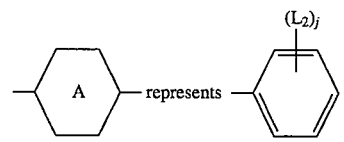

the silacyclohexane-based compound of the foregoing formula (IV) can be obtained.

By the procedures having set out hereinbefore, we can prepare various types of silacyclohexane-based liquid crystal compounds in a trans form or in a trans, trans form having a fluorine substituent at the intended position.

The present invention is more particularly described by way of examples.

EXAMPLE 1

Preparation of (2-fluoro-4-(4-n-pentyl-4-phenyl-4-silacyclohexyl) phenyl) trifluoromethanesulfonate A Grignard reagent was prepared from 30.5 g of 4-bromo-2-fluorophenol t-butyldimethylsilyl ether and 2.43 g of magnesium in 100 ml of tetrahydrofuran. 20.0 g of 4-n-pentyl-4-phenyl-4-silacyclohexanone was dropped in the resultant solution at 25° C. The reaction mixture was agitated at 25° C. for 5 hours and poured into an ammonium chloride aqueous solution, followed by extraction with ethyl acetate. The ethyl acetate solution was washed with brine, dried and concentrated. 400 ml of benzene and 800 mg of p-toluenesulfonic acid monohydrate were added to the resultant residue, followed by removal of generated water under reflux. When distilling of water was stopped, the benzene solution was concentrated, followed by purification of the resultant residue to obtain 31.6 g (yield: 88%) of 2-fluoro-4-(4-n-pentyl-4-phenyl)-4-sila-1-cyclohexnyl)phenol t-butyldimethylsilyl ether.

The thus obtained product was subjected to IR and NMR analyses with the results shown below.

IR (liquid film) $v_{max}$: 2960, 2930, 2855, 1510, 1295, 1255, 1120, 905 cm$^{-1}$ $^1$H-NMR (CDCl$_3$) δ: 0.10–0.30 (6H, m), 0.70–1.80 (15H, m), 1.01 (9H, s), 2.62 (2H, t), 6.13 (2H, t), 6.65–7.64 (8H m) ppm 20.0 g of the ether product was dissolved in 30 ml of ethyl acetate, followed by catalytic reduction in the presence of a palladium-carbon catalyst. When one equivalent of hydrogen was consumed, the catalyst was removed by filtration and the resultant filtrate was concentrated to obtain 20.1 g (quantitative yield) of 2-fluoro-4-(4-n-pentyl-4-phenyl-4-silacyclohexyl)phenol t-butyldimethylsilyl ether.

The thus obtained product was subjected to IR and NMR analyses with the results shown below.

IR (liquid film) $v_{max}$: 2960, 2930, 2855, 1515, 1295, 1255, 1115, 905 cm$^{-1}$ $^1$H-NMR (CDCl$_3$) δ: 0.20–0.35 (6H, m), 0.78–1.90 (26H, m), 2.10–2.32 (2H, m), 2.42–2.58 (1H, m), 6.76–7.70 (8H m) ppm 15.0 g of the above product was dissolved in 100 ml of tetrahydrofuran, followed by addition of 35 ml of a tetrahydrofuran solution of 1.0 mole of tetra-n-butylammonium fluoride and agitation at 20° C. for 2 hours. The reaction mixture was charged into diluted hydrochloric acid and extracted with ether. The ether solution was washed with brine, dried and concentrated and the resultant residue was purified through silica gel chromatography to obtain 11.2 g (yield: 99%) of 2-fluoro-4-(4-n-pentyl-4-phenyl-4-silacyclohexyl)phenol. The results of GC-MS and IR analyses are shown below.

GC-MS (70 eV) (m/z)$^+$: 105, 179, 217, 257, 285, 300, 356 (M$^+$)

IR (liquid film) $v_{max}$: 3400 (broad), 2960, 2920, 2855, 1515, 1270, 1110 cm$^{-1}$ 10.0 g of the product was dissolved in 50 ml of pyridine, followed by dropping 8.20 g of trifluoromethanesulfonic anhydride. After agitation at 0° C. for 5 hours, the reaction mixture was poured into diluted hydrochloric acid and extracted with ether. The ether solution was washed with brine, dried and concentrated and the resultant residue was purified through silica gel chromatography to obtain 10.2 g (yield: 80%) of the intended product. The results of IR and $^1$H-NMR analyses of the product are shown below.

IR (liquid film) $v_{max}$: 2960, 2925, 2855, 1600, 1500, 1425, 1245, 1210, 1140, 1100, 885 cm$^{-1}$ $^1$H-NMR (CDCl$_3$) δ: 0.55–2.70 (20H, m), 6.85–7.66 (8H m) ppm

EXAMPLE 2

Preparation of (2-fluoro-4-(4-phenyl-4-n-propyl-4-silacyclohexyl)phenyl) trifluoromethanesulfonate The general procedure of Example 1 was repeated using 4-phenyl-4-n-propyl-4-silacyclohexanone, thereby obtaining the captioned compound. The results of IR and $^1$H-NMR analyses of the product are shown below.

IR (KBr, disc) $v_{max}$: 2960, 2925, 2860, 1600, 1500, 1425, 1245, 1215, 1140, 1100, 885 cm$^{-1}$ $^1$H-NMR (CDCl$_3$) δ: 0.55–2.70 (16H, m), 6.85–7.66 (8H m) ppm

EXAMPLE 3

Preparation of (2,6-difluoro-4-(4-n-pentyl-4-phenyl-4-silacyclohexyl)phenyl) trifluoromethanesulfonate The general procedure of Example 1 was repeated using 4-bromo-2,6-difluorophenol t-butyldimethylsilyl ether, thereby obtaining the captioned compound.

The results of IR and $^1$H-NMR analyses of the product are shown below.

IR (KBr, disc) $v_{max}$: 2960, 2925, 2860, 1605, 1505, 1430, 1250, 1215, 1140, 1040, 880 cm$^{-1}$ $^1$H-NMR (CDCl$_3$) δ: 0.55–2.65 (20H, m), 6.70–7.70 (7H m) ppm

EXAMPLE 4

Preparation of (2,6-difluoro-4-(4-phenyl-4-n-propyl-4-silacyclohexyl)phenyl) trifluoromethanesulfonate The general procedure of Example 1 was repeated using 4-phenyl-4-n-propyl-4-silacyclohexane and 4-bromo-2,6-difluorophenol t-butyldimethylsilyl ether, thereby obtaining the intended product. The results of IR and $^1$H-NMR analyses of the product are shown below.

IR (liquid film) $v_{max}$: 2958, 2922, 2872, 1608, 1512, 1435, 1252, 1219, 1138, 1043, 879 cm$^{-1}$ $^1$H-NMR (CDCl$_3$) δ: 0.55–2.65 (16H, m), 6.70–7.70 (7H m) ppm

EXAMPLE 5

Preparation of trans-4-(4-n-pentyl-4-silacyclohexyl)-2, 3', 4', 5'-tetrafluorobiphenyl 40 ml of a tetrahydrofuran solution of 0.8 moles of 3,4,5-trifluorophenylzinc chloride prepared by reaction between a corresponding Grignard reagent and zinc chloride was dropped in a mixture of 10.0 g of (2-fluoro-4-(4-n-pentyl-4-phenyl-4-silacyclohexyl)phenyl) trifluoromethanesulfonate, 100 mg of tetrakis(triphenylphosphine)palladium (0), 500 mg of lithium chloride and 50 ml of N,N-dimethylformamide. After agitation at 50° C. for 8 hours, the mixture was charged into an ammonium chloride aqueous solution, followed by extraction with ethyl acetate. The ethyl acetate solution was washed with brine, dried, and concentrated, followed by purification of the resultant residue through silica gel chromatography to obtain 8.20 g (yield: 75%) of 4-(4-n-pentyl-4-phenyl-4-silacyclohexyl)-2,3',4',5'-tetrafluorobiphenyl. The results of IR and $^1$H-NMR analyses of the product are shown below.

IR (liquid film) $v_{max}$: 2960, 2925, 2850, 1615, 1535, 1500, 1405, 1110, 1045 cm$^{-1}$ $^1$H-NMR (CDCl$_3$) δ: 0.60–2.70 (20H, m), 6.80–7.70 (10H, m) ppm 8.00 g of the product was dissolved in 100 ml of carbon tetrachloride, to which 20 ml of a carbon tetrachloride solution of 1.0 mole of iodine monochloride, followed by agitation at room temperature for 2 hours. The reaction mixture was concentrated and the resultant residue was dissolved in 10 ml of tetrahydrofuran. The resultant solution was dropped in a mixture of 800 mg of lithium aluminium hydride and 20 ml of tetrahydrofuran, followed by agitation at 40° C. for 12 hours. The mixture was poured into diluted hydrochloric acid and extracted with methylene chloride, followed by washing with brine, drying and concentration. The resultant residue was purified through silica gel chromatography to obtain 3.20 g (yield: 48%) of the intended product. The results of IR and NMR analyses of the product are shown below.

IR (liquid film) $v_{max}$: 2956, 2920, 2854, 2102, 1618, 1537, 1502, 1406, 1120, 1047, 989, 889, 864, 818 cm$^{-1}$ $^{13}$C-NMR (CDCl$_3$) δ: 10.42 (s), 11.98 (s), 13.96 (s), 22.37 (s), 24.04 (s), 33.04 (s), 35.37 (s), 47.16 (d), 112.92 (d), 114.50 (d), 123.06 (d), 123.32 (s), 129.80 (d), 131.83 (m), 139.15 (dt), 151.08 (dd), 151.79 (d), 159.47 (d) ppm

EXAMPLE 6

Preparation of trans-4-(4-n-pentyl-4-silacyclohexyl)-2, 6, 3', 4'-tetrafluorobiphenyl The general procedure of Example 5 was repeated using 3,4-difluorophenylzinc chloride and (2,6-difluoro-4-(4-n-pentyl-4-phenyl-4-silacyclohexyl)phenyl)trifluoromethanesulfonate, thereby obtaining the intended product. The IR and $^{13}$C-NMR analyses of the product are shown below. The results of IR and NMR analyses of the product are shown below.

IR (KBr, disc) $v_{max}$: 2954, 2918, 2848, 2110, 1639, 1491, 1410, 1200, 1119, 1018, 885, 818 cm$^{-1}$ $^{13}$C-NMR (CDCl$_3$) δ: 10.32 (s), 11.93 (s), 13.95 (s), 22.36 (s), 24.01 (s), 32.89 (s), 35.36 (s), 47.29 (d), 109.99 (d), 113.59 (t), 117.03 (d), 119.46 (d), 126.16 (m), 126.66 (m), 150.02 (dd), 151.48 (t), 159.66 (dd) ppm

EXAMPLE 7

Preparation of
trans-4-(4-n-pentyl-4-silacyclohexyl)-2,
4"-difluoroterphenyl

The general procedure of Example 5 was repeated using 4'-fluorobiphenylzinc chloride, thereby obtaining the intended product. The results of IR and $^{13}$C-NMR analyses of the product are shown below.

IR (KBr, disc) ν$_{max}$: 2956, 2920, 2846, 2106, 1487, 1222, 887, 816 cm$^{-1}$ $^{13}$C-NMR (CDCl$_3$) δ: 10.47 (s), 12.02 (s), 13.99 (s), 22.35 (s), 24.04 (s), 33.10 (s), 35.35 (s), 47.14 (d), 114.28 (d), 115.66 (d), 122.79 (d), 125.67 (d), 126.96 (s), 128.60 (d), 129.33 (d), 130.25 (d), 134.91 (d), 136.85 (d), 139.18 (s), 150.56 (d), 159.75 (d), 162.51 (d) ppm

EXAMPLE 8

Preparation of
trans-4-(4-n-pentyl-4-silacyclohexyl)-2, 3",
4"-trifluoroterphenyl The general procedure of Example 5 was repeated using 3',4'-difluorobiphenylzinc chloride, thereby obtaining the intended product. The results of IR and $^{13}$C-NMR analyses of the product are shown below.

IR (KBr, disc) ν$_{max}$: 2960, 2912, 2848, 2096, 1491, 1396, 1313, 1180, 874, 812 cm$^{-1}$ $^{13}$C-NMR (CDCl$_3$) δ: 10.47 (s), 12.01 (s), 13.99 (s), 22.36 (s), 24.04 (s), 33.10 (s), 35.36 (s), 47.15 (d), 114.31 (d), 115.89 (d), 117.55(d), 122.84 (d), 122.88 (dd), 125.48 (d), 126.91 (s), 129.44 (d), 130.22 (d), 135.51 (s), 137.86 (dd), 138.05 (s), 149.96 (dd), 150.54 (dd), 150.73 (d), 159.74 (d) ppm

EXAMPLE 9

Preparation of trans,
trans-2-fluoro-4-(4-n-pentyl-4-silacyclohexyl)-
4'-(4-n-propylcyclohexyl)biphenyl 80 ml of a tetrahydrofuran solution of 0.5 moles of tributyl(trans-4-(4-n-propylcyclohexyl)phenyl)tin prepared from a corresponding Grignard reagent and tri-n-butyltin chloride was dropped in a mixture of 15.0 g of 2-fluoro-4-(4-n-pentyl-4-silacyclohexyl)phenyl trifluoromethanesulfonate, 250 mg of tetrakis(triphenylphosphine)palladium (0), 2.0 g of lithium chloride and 60 ml of 1,4-dioxane. After agitation at 50° C. for 12 hours, the resultant product was treated and purified in the same manner as in Example 5 to obtain 14.3 g (yield: 80%) of 2-fluoro-4-(4-n-pentyl-4-phenyl-4-silacyclohexyl)-4'-(trans-4-n-propylcyclohexyl-)biphenyl. The results of the IR and NMR analyses of the product are shown below.

IR (KBr, disc) ν$_{max}$: 2960, 2925, 2850, 1490, 1425, 1400, 1115, 980 cm$^{-1}$ $^1$H-NMR (CDCl$_3$) δ: 0.70–2.70 (37H, m), 6.76–7.65 (12H, m) ppm The thus obtained product was reacted first with iodine monochloride and then with lithium aluminium hydride to obtain the intended compound with the following results of IR and NMR analyses.

IR (KBr, disc) ν$_{max}$: 2952, 2920, 2848, 2098, 1492, 1404, 1194, 987, 887, 812 cm$^{-1}$ $^{13}$C-NMR (CDCl$_3$) δ: 10.47 (s), 12.04 (s), 13.99 (s), 14.42 (s), 20.03 (s), 22.36 (s), 24.04 (s), 33.11 (s), 33.58 (s), 34.29 (s), 35.37 (s), 37.04 (s), 39.74 (s), 44.34 (s), 47.10 (s), 114.13 (d), 122.6 (d), 126.21 (d), 126.85 (s), 128.76 (d), 130.30 (d), 133.33 (s), 147.03 (s), 149.97 (d), 159.70 (d) ppm

EXAMPLE 10

Preparation of trans,
trans-2-fluoro-4-(4-n-propyl-4-silacyclohexyl)-
4'-(4-n-pentylcyclohexyl)biphenyl The general procedure of Example 9 was repeated using tributyl(trans-4-(4-n-pentylcyclohexyl)phenyl)tin and 2-fluoro-4-(4-n-propyl-4-silacyclohexyl)phenyl trifluoromethanesulfonate, thereby obtaining the captioned product. The results of the IR and NMR analyses are shown below.

IR (KBr, disc) ν$_{max}$: 2954, 2920, 2850, 2102, 1446, 1404, 1194, 987, 887, 814 cm$^{-1}$ $^{13}$C-NMR (CDCl$_3$) δ: 10.51 (s), 14.12 (s), 14.63 (s), 17.79 (s), 17.89 (s), 22.73 (s), 26.67 (s), 32.24 (s), 33.11 (s), 33.63 (s), 34.31 (s), 37.34 (s), 37.41 (s), 44.35 (s), 47. 10 (s), 114.14 (d), 122.62 (d), 126.21 (d), 126.86 (s), 128.77 (d), 130.31 (d), 133.33 (s), 147.06 (s), 149.97 (d), 159.71 (d) ppm

EXAMPLE 11

Preparation of trans,
trans-2-fluoro-4-(4-n-propyl-4-silacyclohexyl)-
4'-(4-n-propylcyclohexyl)biphenyl The general procedure of Example 9 was repeated using (2-fluoro-4-(4-n-propyl-4-phenyl-4-silacyclohexyl)phenyl) trifluoromethanesulfonate, thereby obtaining the captioned product. The results of the IR and NMR analyses are shown below.

IR (KBr, disc) ν$_{max}$: 2954, 2920, 2848; 2104, 1491, 1404, 1194, 985, 889, 814 cm$^{-1}$ $^{13}$C-NMR (CDCl$_3$) δ: 10.49 (s), 14.42 (s), 14.62 (s), 17.79 (s), 17.89 (s), 20.03 (s), 33.11 (s), 33.58 (s), 34.29 (s), 37.03 (s), 39.74 (s), 44.35 (s), 47.10 (s), 114.13 (d), 122.63 (d), 126.21 (d), 126.86 (s), 128.77 (d), 130.31 (d), 133.34 (s), 147.06 (s), 149.99 (d), 159.70 (d) ppm

EXAMPLE 12

Preparation of trans,
trans-2-fluoro-4-(4-n-pentyl-4-silacyclohexyl)-
4'-(4-n-pentylcyclohexyl)biphenyl The general procedure of Example 9 was repeated using tributyl(trans-4(4-n-pentylcyclohexyl)phenyl)tin, thereby obtaining the captioned product. The results of the IR and NMR analyses are shown below.

IR (KBr, disc) ν$_{max}$: 2954, 2920, 2848, 2100, 1491, 1404, 1194, 987, 887, 814 cm$^{-1}$ $^{13}$C-NMR (CDCl$_3$) δ: 10.47 (s), 12.04 (s), 13.99 (s), 14.12 (s), 22.35 (s), 22.72 (s), 24.04 (s), 26.66 (s), 32.22 (s), 33.11 (s), 33.62 (s), 34.30 (s), 35.36 (s), 37.33 (s), 37.40 (s), 44.35

(s), 47.10 (s), 114.14 (d), 122.65 (d), 126.21 (d), 126.86 (s), 128.77 (d), 130.31 (d), 133.35 (s), 147.07 (s), 150.00 (d), 159.70 (d) ppm

EXAMPLE 13

Preparation of trans-2-fluoro-4-(4-n-pentyl-4-silacyclohexyl)-4'-(2-(4-fluorophenyl)ethyl)biphenyl The general procedure of Example 9 was repeated using tributyl(4-(2-(4-fluorophenyl)ethyl)phenyl)tin, thereby obtaining the captioned product. The results of the IR and NMR analyses are shown below.

IR (KBr, disc) $v_{max}$: 2956, 2916, 2850, 2104, 1508, 1493, 1404, 1221, 987, 887, 816 cm$^{-1}$ $^{13}$C-NMR (CDCl$_3$) δ: 10.46 (s), 12.02 (s), 13.99 (s), 22.35 (s), 24.04 (s), 33.10 (s), 35.35 (s), 36.94 (s), 37.71 (s), 47.10 (s), 114.18 (d), 115.04 (d), 122.65 (s), 126.04 (d), 128.47 (s), 128.86 (d), 129.79 (d), 130.27 (d), 133.01 (s), 137.26 (d), 140.61 (s), 150.18 (d), 159.69 (d), 161.32 (d) ppm

EXAMPLE 14

Preparation of trans-2-fluoro-4-(4-n-pentyl-4-silacyclohexyl)-4'-(2-(3,4-difluorophenyl)ethyl)biphenyl The general procedure of Example 9 was repeated using tributyl(4-(2-(3,4-difluorophenyl)ethyl)phenyl)tin, thereby obtaining the captioned product. The results of the IR and NMR analyses are shown below.

IR (KBr, disc) $v_{max}$: 2956, 2920, 2848, 2102, 1518, 1491, 1404, 1290, 1286, 1120, 889, 818 cm$^{-1}$ $^{13}$C-NMR (CDCl$_3$) δ: 10.15 (s), 11.73 (s), 13.65 (s), 22.08 (s), 23.78 (s), 32.83 (s), 35.10 (s), 36.53 (s), 36.99 (s), 46.82 (d), 113.85 (s), 116.56 (d), 116.80 (d), 122.39 (d), 123.96 (dd), 125.69 (d), 128.11 (s), 128.57 (d), 129.95 (d), 133.47 (d), 138.31 (dd), 139.83 (s), 148.49 (dd), 149.49 (dd), 149.82 (dd), 149.88 (d), 159.42 (d) ppm As will be apparent from the foregoing examples, the triflate compounds of the invention are useful as an intermediate for preparing silacyclohexane-based liquid crystal compounds.

What is claimed is:

1. A triflate compound of the following formula (I)

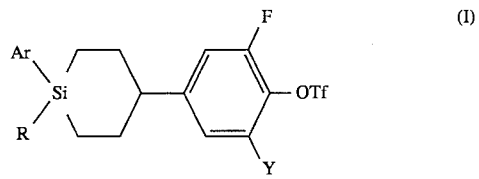

wherein Ar represents a phenyl group or a tolyl group, R represents a phenyl group, a tolyl group, a linear alkyl group having from 1 to 10 carbon atoms, a mono or difluoroalkyl group having from 1 to 10 carbon atoms, a branched alkyl group having from 3 to 8 carbon atoms, an alkoxyalkyl group having from 2 to 7 carbon atoms or an alkenyl group having from 2 to 8 carbon atoms, Tf represents a trifluoromethanesulfonyl group, and Y represents H or F.

2. A process for preparing a silacyclohexane-based liquid crystal compound which comprises the steps of:

(1) subjecting a triflate compound of the general formula (I)

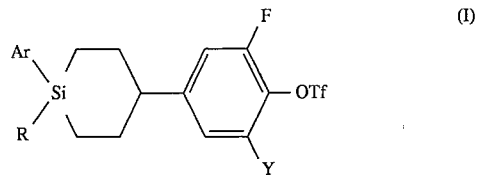

wherein Ar represents a phenyl group or a tolyl group, R represents a phenyl group, a tolyl group, a linear alkyl group having from 1 to 10 carbon atoms, a mono or difluoroalkyl group having from 1 to 10 carbon atoms, a branched alkyl group having from 3 to 8 carbon atoms, an alkoxyalkyl group having from 2 to 7 carbon atoms or an alkenyl group having from 2 to 8 carbon atoms, Tf represents a trifluoromethanesulfonyl group, and Y represents H or F, to reaction with an organometallic reagent of the following general formula in the presence of a transition metal catalyst

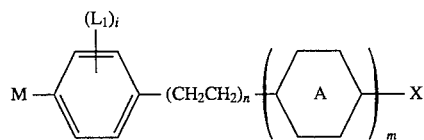

wherein

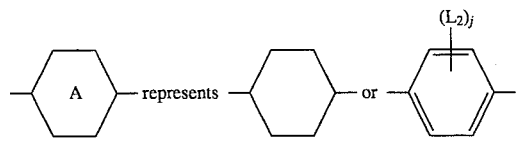

in which $L_2$ represents a halogen or CH$_3$, and j is a value of 0, 1 or 2, M represents ZnP, in which P represents a halogen, Sn(CH$_2$CH$_2$CH$_2$CH$_3$)$_3$ or Sn(CH$_3$)$_3$, X represents R or OR, in which each R has the same meaning as defined above, CN, F, Cl, Br, CF$_3$, OCF$_3$, OCHF$_2$, OCHFCl, OCF$_2$Cl, CF$_2$Cl, CHFCl, (O)m$_1$CY$_1$=CX$_1$CX$_2$, in which m1 is a value of 0 or 1, Y$_1$ and X$_1$ independently represent H, F or Cl, and X$_2$ represents F or Cl, or O(CH$_2$)$_r$(CF$_2$)$_s$X$_3$, in which r and s are, respectively, a value of 0, 1 or 2 provided that r+s=2,3 or 4, and X$_3$ represents H, F or Cl, L$_1$ represents a halogen or CH$_3$, n and m are, respectively, a value of 0 or 1, and i is a value of 0, 1 or 2, thereby obtaining a compound of the following general formula

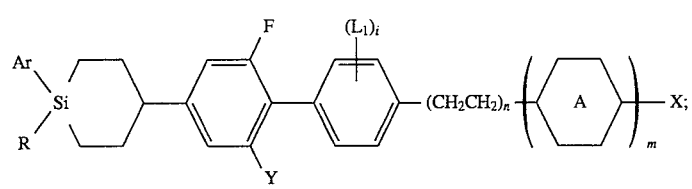

and (2) subjecting the compound of the above formula to de-silylation and then to reduction to obtain a silacyclohexane-based compound of the formula

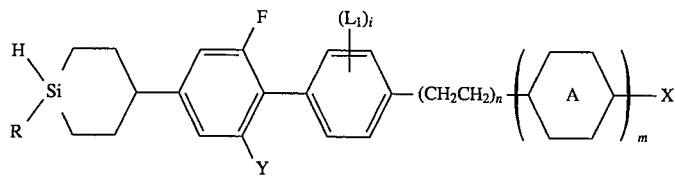

wherein

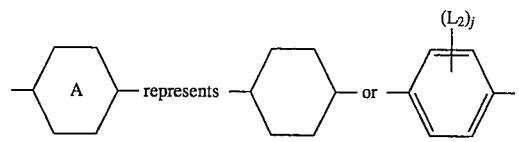

in which $L_2$ represents a halogen or $CH_3$, and j is a value of 0,1 or 2, R, $L_1$, i, Y, X, n and m have, respectively the same meanings as defined above.

3. A process according to claim 2, wherein further adding a lithium salt to the step (1) whereby the reaction is facilitated.

4. A process according to claim 2, wherein the de-silylation in step (2) is effected by further addition of a Lewis acid or by irradiation of visible light or UV light.

5. A process according to claim 2, wherein said organometallic reagent is of the following formula

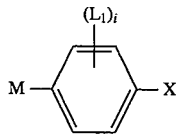

wherein M, $L_1$, i and X have, respectively, the same meanings as defined in claim 2, whereby the resultant silacyclohexane-based compound has the following general formula (II)

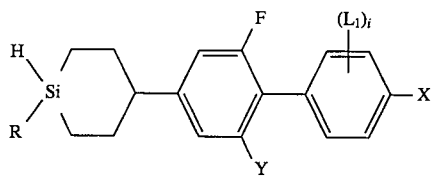

wherein R, Y, X, $L_1$ and i have, respectively, the same meanings as defined in claim 2.

6. A process according to claim 2, wherein said organometallic reagent is of the following formula

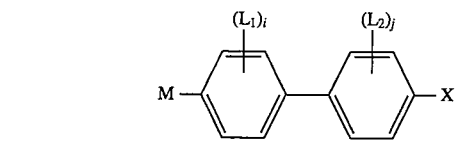

wherein M, $L_1$, $L_2$, X, i and j have, respectively, the same meanings as defined in claim 2, whereby the resultant silacyclohexane-based compound has the following general formula (III)

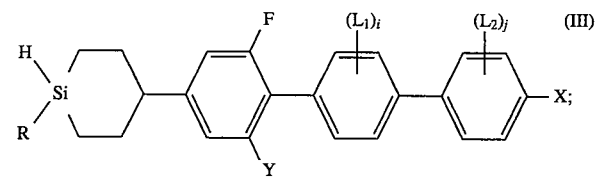

wherein R, Y, X, $L_1$, $L_2$, i and j have, respectively, the same meanings as defined in claim 2.

7. A process according to claim 2, wherein said organometallic reagent is of the following formula

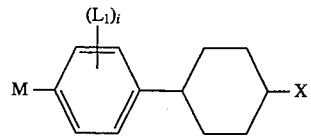

wherein M, $L_1$, X and i have, respectively, the same meanings as defined above, whereby the resultant silacyclohexane-based compound has the following general formula (IV)

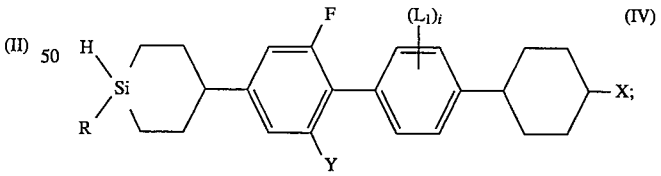

wherein R, Y, X, $L_1$, and i have, respectively, the same meanings as defined in claim 2.

* * * * *